United States Patent
Adachi

(10) Patent No.: US 10,660,606 B2
(45) Date of Patent: May 26, 2020

(54) ULTRASONIC IMAGING APPARATUS AND METHOD OF CONTROLLING ULTRASONIC IMAGING APPARATUS

(71) Applicant: SOCIONEXT INC., Yokohama-shi, Kanagawa (JP)

(72) Inventor: Naoto Adachi, Yokohama (JP)

(73) Assignee: SOCIONEXT INC., Yokohama (JP)

( * ) Notice: Subject to any disclaimer, the term of this patent is extended or adjusted under 35 U.S.C. 154(b) by 317 days.

(21) Appl. No.: 15/725,918

(22) Filed: Oct. 5, 2017

(65) Prior Publication Data
US 2018/0042574 A1 Feb. 15, 2018

Related U.S. Application Data

(63) Continuation of application No. PCT/JP2016/060619, filed on Mar. 31, 2016.

(30) Foreign Application Priority Data

Apr. 17, 2015 (JP) .................................. 2015-084827

(51) Int. Cl.
*A61B 8/14* (2006.01)
*G01S 15/89* (2006.01)
(Continued)

(52) U.S. Cl.
CPC .............. *A61B 8/14* (2013.01); *A61B 8/4488* (2013.01); *A61B 8/4494* (2013.01); *A61B 8/488* (2013.01);
(Continued)

(58) Field of Classification Search
CPC ....... A61B 8/14; A61B 8/5207; A61B 8/4488; A61B 8/488; A61B 8/4494; G01S 7/52026; G01S 15/8915; G10K 11/346
See application file for complete search history.

(56) References Cited

U.S. PATENT DOCUMENTS

| | | | | |
|---|---|---|---|---|
| 4,155,258 A | * | 5/1979 | Engeler | G01N 29/06 367/7 |
| 4,837,754 A | * | 6/1989 | Nakagawa | G01S 7/52046 367/103 |
| 5,831,168 A | * | 11/1998 | Shinomura | G01N 29/0609 73/602 |

FOREIGN PATENT DOCUMENTS

JP   S54-096066 A   7/1979
JP   S56-020016 B   5/1981
(Continued)

OTHER PUBLICATIONS

International Search Report of related International Patent Application No. PCT/JP2016/060619 dated May 31, 2016. (With partial English information).

*Primary Examiner* — Bo Joseph Peng
(74) *Attorney, Agent, or Firm* — Arent Fox LLP

(57) ABSTRACT

An ultrasonic imaging apparatus includes a plurality of transducers aligned in an array, a select circuit configured to cause transducers selected from the plurality of transducers to transmit an ultrasonic pulse and receive received signals, respectively, and a digital signal processing circuit configured to perform a first operation of adding up an odd number of the received signals, arranged in an order corresponding to the aligned array, with delays that are symmetrical between two sides across a center that is a centrally located signal, and to perform a second operation of adding up an even number of the received signals, arranged in an order corresponding to the aligned array, with delays that are symmetrical between two sides across a center that is situated between two centrally located signals.

6 Claims, 11 Drawing Sheets

(51) Int. Cl.
   *A61B 8/00*   (2006.01)
   *G10K 11/34*  (2006.01)
   *A61B 8/08*   (2006.01)
   *G01S 7/52*   (2006.01)

(52) U.S. Cl.
   CPC ........ *A61B 8/5207* (2013.01); *G01S 7/52026* (2013.01); *G01S 15/8915* (2013.01); *G10K 11/346* (2013.01)

(56) References Cited

FOREIGN PATENT DOCUMENTS

| | | |
|---|---|---|
| JP | H10-118063 A | 5/1998 |
| JP | 2009-142680 A | 7/2009 |

\* cited by examiner

FIG.9

| DEPTH [mm] | CHANNEL1 [ns] | CHANNEL2 [ns] | CHANNEL3 [ns] | CHANNEL4 [ns] | CHANNEL5 [ns] | CHANNEL6 [ns] | CHANNEL7 [ns] | CHANNEL8 [ns] |
|---|---|---|---|---|---|---|---|---|
| 10 | 0 | 83.74 | 140.16 | 168.56 | 168.56 | 140.16 | 83.74 | 0 |
| 20 | 0 | 42.49 | 70.9 | 85.12 | 85.12 | 70.9 | 42.49 | 0 |
| 30 | 0 | 28.41 | 47.37 | 56.86 | 56.86 | 47.37 | 28.41 | 0 |
| 40 | 0 | 21.33 | 35.55 | 42.67 | 42.67 | 35.55 | 21.33 | 0 |
| 50 | 0 | 17.07 | 28.45 | 34.15 | 34.15 | 28.45 | 17.07 | 0 |
| 60 | 0 | 14.23 | 23.72 | 28.46 | 28.46 | 23.72 | 14.23 | 0 |
| 70 | 0 | 12.2 | 20.33 | 24.4 | 24.4 | 20.33 | 12.2 | 0 |
| 80 | 0 | 10.67 | 17.79 | 21.35 | 21.35 | 17.79 | 10.67 | 0 |
| 90 | 0 | 9.49 | 15.81 | 18.98 | 18.98 | 15.81 | 9.49 | 0 |
| 100 | 0 | 8.54 | 14.23 | 17.08 | 17.08 | 14.23 | 8.54 | 0 |

FIG.10

| DEPTH [mm] | CHANNEL1 [ns] | CHANNEL2 [ns] | CHANNEL3 [ns] | CHANNEL4 [ns] | CHANNEL5 [ns] | CHANNEL6 [ns] | CHANNEL7 [ns] |
|---|---|---|---|---|---|---|---|
| 10 | 0 | 70.19 | 112.67 | 126.89 | 112.67 | 70.19 | 0 |
| 20 | 0 | 35.46 | 56.79 | 63.90 | 56.79 | 35.46 | 0 |
| 30 | 0 | 23.69 | 37.91 | 42.66 | 37.91 | 23.69 | 0 |
| 40 | 0 | 17.78 | 28.45 | 32.01 | 28.45 | 17.78 | 0 |
| 50 | 0 | 14.23 | 22.77 | 25.61 | 22.77 | 14.23 | 0 |
| 60 | 0 | 11.86 | 18.97 | 21.35 | 18.97 | 11.86 | 0 |
| 70 | 0 | 10.17 | 16.27 | 18.30 | 16.27 | 10.17 | 0 |
| 80 | 0 | 8.90 | 14.23 | 16.01 | 14.23 | 8.90 | 0 |
| 90 | 0 | 7.91 | 12.65 | 14.23 | 12.65 | 7.91 | 0 |
| 100 | 0 | 7.12 | 11.39 | 12.81 | 11.39 | 7.12 | 0 |

ULTRASONIC IMAGING APPARATUS AND METHOD OF CONTROLLING ULTRASONIC IMAGING APPARATUS

CROSS-REFERENCE TO RELATED APPLICATIONS

This application is a continuation application of International Application PCT/JP2016/060619, filed on Mar. 31, 2016 and designated the U.S., which is based upon and claims the benefit of priority from the prior Japanese Patent Application No. 2015-084827 filed on Apr. 17, 2015, with the Japanese Patent Office. The entire contents of these applications are incorporated herein by reference.

BACKGROUND OF THE INVENTION

1. Field of the Invention

The disclosures herein relate to an ultrasonic imaging apparatus and a method of controlling an ultrasonic imaging apparatus.

2. Description of the Related Art

An ultrasonic imaging apparatus such as an ultrasound image diagnosis apparatus has a pulse circuit to apply a pulse voltage signal to a transducer. In response to the pulse voltage signal, the transducer transmits an ultrasonic pulse into a living body. The ultrasonic pulse reflects off the boundary between different living tissues having different acoustic impedances such as a boundary between muscle and fat. The echo is then received by the transducer. A received signal obtained through a single ultrasonic pulse transmission has an amplitude that changes with time. A temporal position in the received signal corresponds to the distance from the transducer to the reflection point in the living body. The amplitude of the received signal corresponds to the magnitude of reflection at the reflection point in the living body. The received signal having the amplitude changing with time that is obtained through a single ultrasonic pulse transmission is displayed on the screen as a bright line having spatial brightness fluctuations that corresponds to a single scan line. A plurality of received signals that are obtained by successively shifting the position of ultrasonic pulse transmission in a horizontal direction are displayed with respective positional shifts on the screen as a plurality of bright lines corresponding to a plurality of scan lines, thereby forming an ultrasound B-mode image.

A transducer array having a large number of transducer elements (i.e., piezoelectric elements) that may be arranged in one dimension, for example, is utilized to scan ultrasonic pulses. Transmission of a single ultrasonic pulse is performed by simultaneously driving m transducer elements among n (m<n) transducer elements arranged in a line. In so doing, pulse voltage signals having slight timing displacements relative to one another may be applied to the m transducer elements to cause the m transducer elements to transmit ultrasonic pulses at slightly different timings. This arrangement allows the transmission aperture having a span corresponding to the m transducer elements to form an ultrasonic beam having a wavefront converging toward a focal point. The position of the m transducer elements driven among the n transducer elements is successively shifted along the one dimensional array, thereby scanning the ultrasonic beam in the lateral direction (i.e., in the direction in which the transducer elements are aligned).

In order to receive echoes, the same m transducer elements that have been used for ultrasonic transmission may be used to receive the echoes. The m transducer elements outputs m received analog signals, respectively, which are then converted into received digital signals by m ADCs (i.e., analog-to-digital converters). The m received digital signals are subjected to delay adjustment such as to eliminate time differences between these signals that are attributable to differences in the distance between the focal point and the m transducer elements. Timing adjustment is thus enabled such that all the received signals have the signal of the echo from the focal point positioned at the same temporal position. All the m received digital signals after the delay adjustment are added up to produce one received digital signal as the result of summation. This one received digital signal is further subjected to noise reduction, gain correction, envelop detection, and the like. The resultant digital signal obtained through these processes may then be displayed on the screen as a single bright line constituting an ultrasound B-mode image.

Recently, there has been an expectation for a mobile version of an ultrasonic imaging apparatus, which has prompted efforts to reduce the size and power consumption of apparatus. The purpose of reducing the size and power consumption of apparatus may be attained by reducing the number of ADCs or by lowering the drive voltage of transducers. In a typical expensive ultrasound image diagnosis apparatus for medical use, the number of ADC channels, i.e., the number of transducer elements simultaneously driven for transmission and reception, may be 32 or 64, for example, which provides an ultrasonic beam having high focusing ability that provides a high-quality image. Reducing the number of ADC channels, i.e., the number of simultaneously driven transducer elements, for the purposes of size reduction and lower power consumption may degrade image quality because of the weakened combined intensity of ultrasonic pulses and received signals. Further, reducing the drive voltage for transducers for the purpose of lower power consumption causes the magnitude of transmitted ultrasonic pulses and received signals of each transducer element to be weakened, resulting in the degradation of image quality. Especially, reducing the number of ADC channels, i.e., the number of simultaneously driven transducer elements, gives rise to the problems of lower focusing ability and degraded resolution.

Accordingly, it may be desired to provide an ultrasonic imaging apparatus for which resolution is increased to improve image quality.

RELATED-ART DOCUMENTS

Patent Document

[Patent Document 1] Japanese Laid-open Patent Publication No. 2009-142680

SUMMARY OF THE INVENTION

According to an embodiment, an ultrasonic imaging apparatus includes a plurality of transducers aligned in an array, a select circuit configured to cause transducers selected from the plurality of transducers to transmit an ultrasonic pulse and receive received signals, respectively, and a digital signal processing circuit configured to perform a first operation of adding up an odd number of the received signals, arranged in an order corresponding to the aligned array, with delays that are symmetrical between two sides across a center that is a centrally located signal, and to perform a second operation of adding up an even number of the received signals, arranged in an order corresponding to the aligned array, with delays that are symmetrical between two sides across a center that is situated between two centrally located signals.

According to an embodiment, an ultrasonic imaging apparatus alternately performs a first operation and a second operation, the first operation coherently adding received signals obtained by causing an odd number of transducers among a plurality of transducers aligned in a line to transmit and receive ultrasonic waves, and the second operation coherently adding received signals obtained by causing an even number of transducers among the plurality of transducers to transmit and receive ultrasonic waves.

According to an embodiment, a method of controlling an ultrasonic imaging apparatus includes performing the steps of causing transducers selected from a plurality of transducers aligned in an array to transmit an ultrasonic pulse and receive first received signals, respectively, adding up an odd number of the first received signals arranged in an order corresponding to the aligned array with delays that are symmetrical between two sides across a center that is a centrally located signal, causing transducers selected from the plurality of transducers aligned in an array to transmit an ultrasonic pulse and receive second received signals, respectively, and adding up an even number of the second received signals arranged in an order corresponding to the aligned array with delays that are symmetrical between two sides across a center that is situated between two centrally located signals.

BRIEF DESCRIPTION OF THE DRAWINGS

FIG. 9 is a drawing illustrating an example of delay times of 8 channels for different focal points;
FIG. 10 is a drawing illustrating an example of delay times of 7 channels for different focal points.

DESCRIPTION OF THE PREFERRED EMBODIMENTS

In the following, embodiments of the invention will be described with reference to the accompanying drawings. In these drawings, the same or corresponding elements are referred to by the same or corresponding numerals, and a description thereof will be omitted as appropriate.

Figure 1:
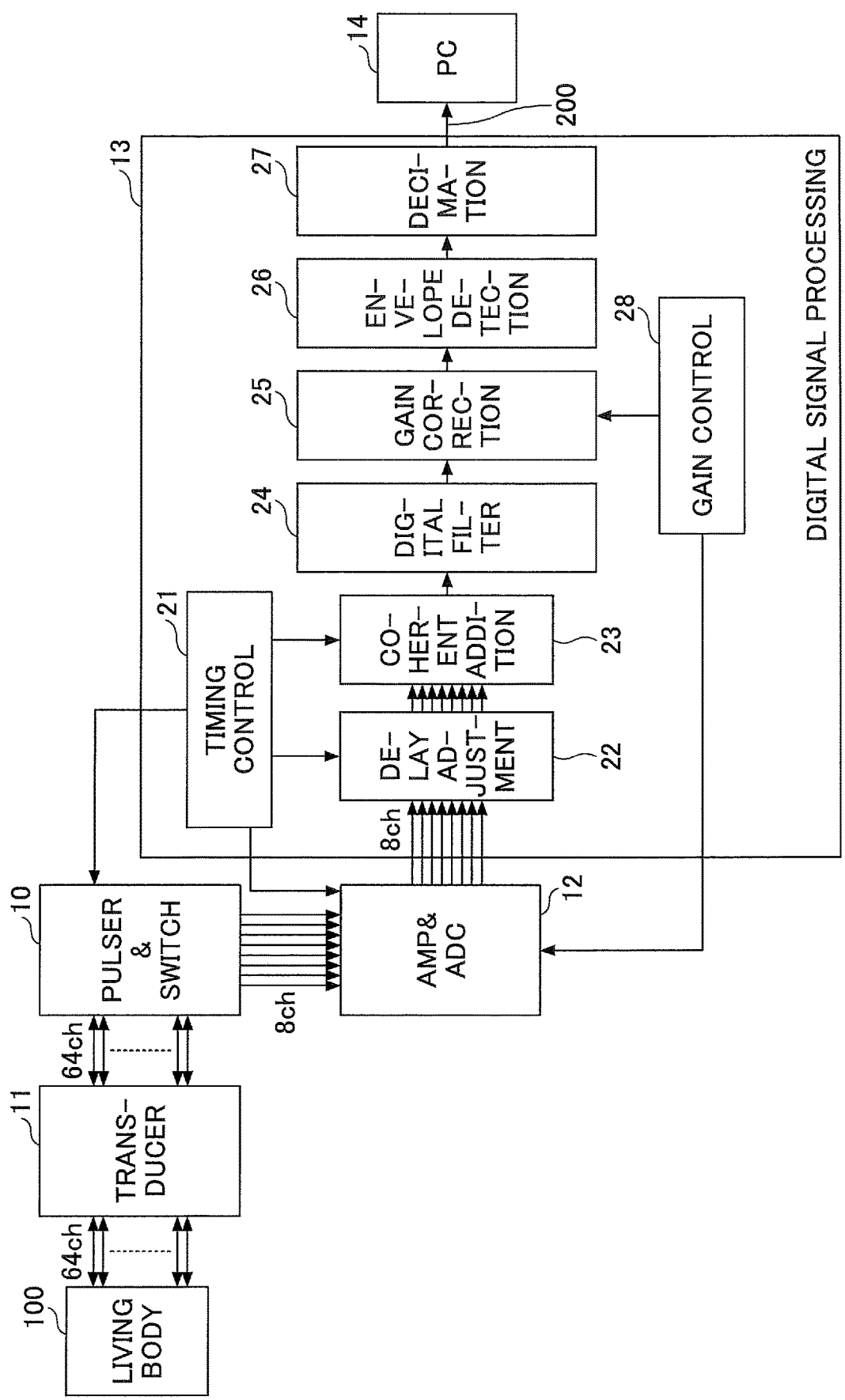
FIG. 1 is a drawing illustrating an example of the configuration of an ultrasonic imaging apparatus.

FIG. 1 is a drawing illustrating an example of the configuration of an ultrasonic imaging apparatus. The ultrasonic imaging apparatus illustrated in FIG. 1 includes a pulser-and-switch circuit 10, a transducer array 11, an amplifier-and-AD-converter circuit (AMP&ADC) 12, and a digital signal processing circuit 13. The digital signal processing circuit 13 includes a timing control circuit 21, a delay adjustment circuit 22, a coherent addition circuit 23, a digital filter 24, a gain correction circuit 25, an envelope detecting circuit 26, a decimating circuit 27, and a gain control circuit 28. Data of ultrasound B-mode image of a living body 100 generated by the ultrasonic imaging apparatus may be transmitted to an information processing and display apparatus such as a personal computer (PC) 14 or a tablet through an interface 200 such as Bluetooth.

In FIG. 1 and the subsequent similar drawings, boundaries between functional or circuit blocks illustrated as boxes basically indicate functional boundaries, and may not correspond to separation in terms of physical positions, separation in terms of electrical signals, separation in terms of control logic, etc. Each functional or circuit block may be a hardware module that is physically separated from other blocks to some extent, or may indicate a function in a hardware module in which this and other blocks are physically combined together.

The transducer array 11 has a plurality (64 in the example illustrated in FIG. 1) of transducer elements arranged in a line. The pulser-and-switch circuit 10 causes a plurality (e.g., 7 or 8) of transducer elements selected from the plurality of transducer elements of the transducer array 11 arranged in a line to transmit an ultrasonic pulse and receive an echo signal. Specifically, under the control of the timing control circuit 21 of the digital signal processing circuit 13, the pulser-and-switch circuit 10 applies pulse voltage signals to the plurality of selected transducer elements consecutively arranged in the alignment direction of the transducer array 11. In response to the pulse voltage signals, the plurality of transducer elements transmits an ultrasonic pulse into the living body 100. The ultrasonic pulse reflects off the boundary between different living tissues having different acoustic impedances such as a boundary between muscle and fat. The echo is then received by the above-noted selected transducer elements.

Transmission of a single ultrasonic pulse is performed by simultaneously driving, among n (e.g., 64) transducer elements arranged in a line, m (m<n) transducer elements. This number m may be 8 or 7, for example. The operation of selectively driving 8 transducer elements, for example, and the operation of selectively driving 7 transducer elements, for example, will be described later in detail. When the operation of selectively driving 8 transducer elements, for example, and the operation of selectively driving 7 transducer elements, for example, are performed, the operation of selectively driving 7 transducer elements allows power consumption to be lowered, compared with the operation of selectively driving 8 transducer elements.

In the case of m transducer elements being driven together, pulse voltage signals having slight timing displacements relative to one another are applied to these m transducer elements, thereby causing the m transducer elements to transmit ultrasonic pulses at respective, slightly different timings. This arrangement allows the transmission aperture having a span corresponding to the m transducer elements to form an ultrasonic beam having a wavefront converging toward a focal point. The position of m transducer elements driven among the n transducer elements of the transducer array 11 is successively shifted along the one dimensional array, thereby scanning the ultrasonic beam in the lateral direction (i.e., in the direction in which the transducer elements are aligned). The timing at which the pulse voltage signals are applied to the m transducer elements may be controlled by the timing control circuit 21 of the digital signal processing circuit 13.

In order to receive echoes, the same m transducer elements that have been used for ultrasonic transmission may be used to receive the echoes. The m received analog signals output from the m transducer elements are supplied to and amplified by the amplifier-and-AD-converter circuit 12, followed by being converted into received digital signals by the m ADCs (i.e., analog-to-digital converters) of the amplifier-and-AD-converter circuit 12. The amplifier-and-AD-converter circuit 12 then supplies the converted received digital signals to the delay adjustment circuit 22 of the digital signal processing circuit 13.

The m received digital signals are subjected to delay adjustment by the delay adjustment circuit 22 such as to eliminate time differences between these signals that are attributable to differences in the distance between the focal point and the m transducer elements. Timing adjustment is thus enabled such that all the received signals have the signal of the echo from the focal point positioned at the same temporal position. All the m received digital signals after the delay adjustment are added up by the coherent addition circuit 23 to produce one received digital signal as the result of summation. This one received digital signal is then subjected to noise removal by the digital filter 24, gain correction by the gain correction circuit 25, envelop detection by the envelope detecting circuit 26, and the like. The decimating circuit 27 selects subsample scan lines or subsample pixels according to need, thereby to generate image data suitable for the format of image display.

The gain correction circuit 25 operates under the control of the gain control circuit 28 so as to amplify the amplitude of a received digital signal such that the later the position of a point of interest in the received signal is, the greater the corresponding amplification factor is. Namely, as the distance from the transducer array 11 to a point of reflection in the living body 100 increases, the amplification factor to amplify the amplitude of a signal received from that point increases.

In the ultrasonic imaging apparatus illustrated in FIG. 1, a first operation of selectively driving 7 transducer elements, for example, and a second operation of selectively driving 8 transducer elements, for example, may be alternately performed under the control of the digital signal processing circuit 13. In the first operation, an odd number of received signals arranged in an order corresponding to the aligned array of the transducer elements of the transducer array 11 are added up after being given respective delays that are symmetrical between the two sides across the centrally situated signal. In the second operation, an even number of received signals arranged in an order corresponding to the aligned array of the transducer elements of the transducer array 11 are added up after being given respective delays that are symmetrical between the two sides across a center that is situated between the two centrally situated signals.

Figure 2:
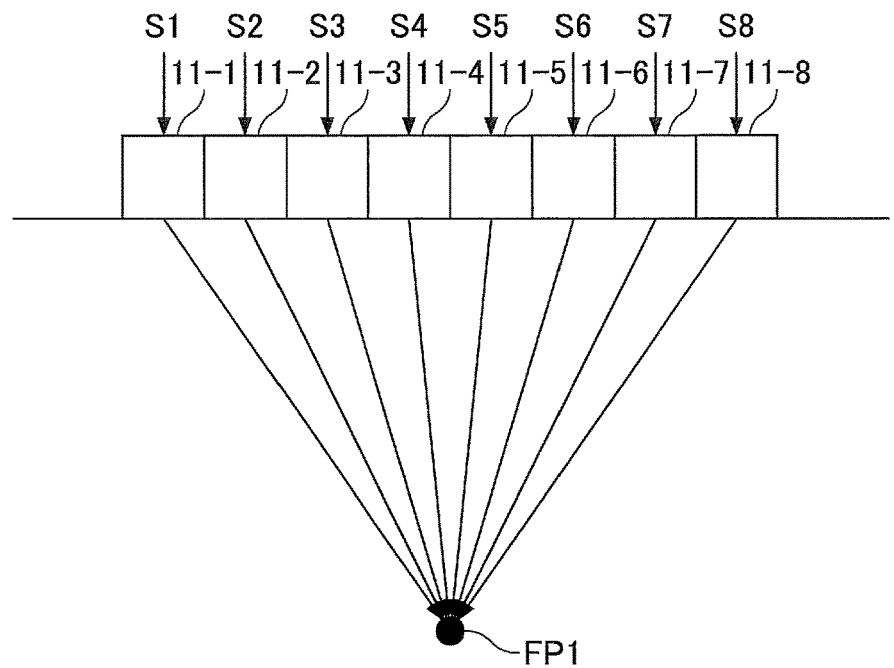
FIG. 2 is a drawing illustrating an example of a transmission operation for which 8 transducer elements are selectively driven.

FIG. 2 is a drawing illustrating an example of a transmission operation for which 8 transducer elements are selectively driven. In FIG. 2, transducer elements 11-1 through 11-8 are 8 consecutive transducer elements among a plurality (e.g., 64) of transducer elements of the transducer array 11 arranged in a line. As pulse voltage signals S1 through S8 are applied to the 8 transducer elements 11-1 through 11-8, respectively, the transducer elements 11-1 through 11-8 transmit an ultrasonic pulse toward a focal point FP1. In so doing, the pulse voltage signals S1 and S8 are first applied to the transducer elements 11-1 and 11-8 situated at the opposite ends, respectively. Upon the passage of a predetermined delay time thereafter, the pulse voltage signals S2 and S7 are applied to the transducer elements 11-2 and 11-7, respectively, which are the second ones from the opposite ends. Upon the passage of a predetermined delay time thereafter, the pulse voltage signals S3 and S6 are applied to the transducer elements 11-3 and 11-6, respectively, which are the third ones from the opposite ends. Upon the passage of a predetermined delay time thereafter, the pulse voltage signals S4 and S5 are applied to the transducer elements 11-4 and 11-5, respectively, which are the fourth ones from the opposite ends. Namely, the transducer elements 11-1 through 11-8 of the transducer array 11 transmit an ultrasonic pulse with respective delays that are symmetrical between the two sides across the center which is situated between the two centrally located elements, such that the closer to the center the transducer element is, the greater the delay is. This arrangement allows the transducer elements 11-1 through 11-8 to transmit an ultrasonic pulse having a wavefront converging toward the focal point FS1.

Figure 3:
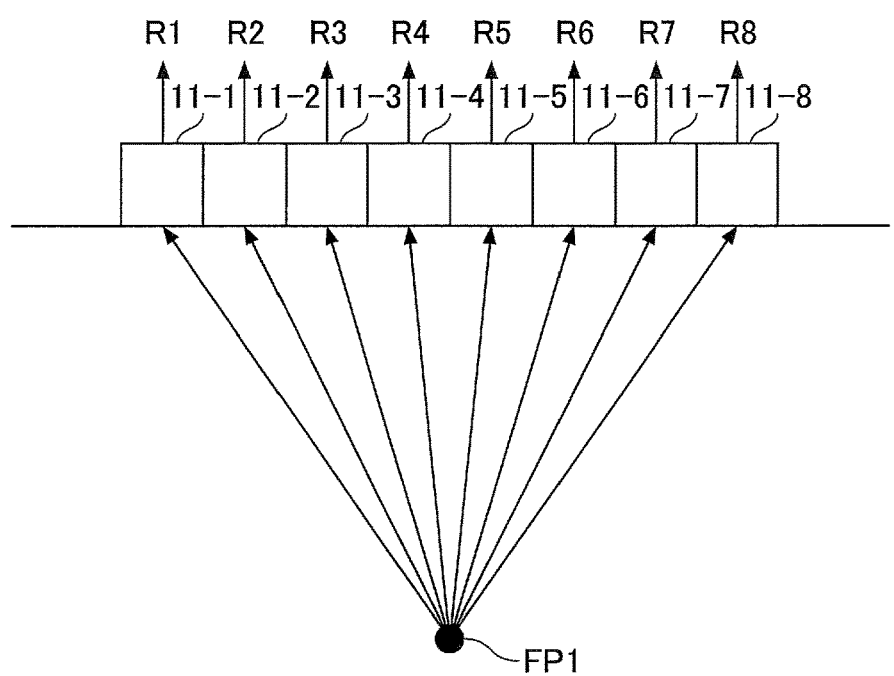
FIG. 3 is a drawing illustrating an example of a reception operation for which 8 transducer elements are selectively driven.

FIG. 3 is a drawing illustrating an example of a reception operation for which 8 transducer elements are selectively driven. In FIG. 3, the transducer elements 11-1 through 11-8, which are 8 consecutive transducer elements among a plurality (e.g., 64) of transducer elements of the transducer array 11 arranged in a line, receive echoes from the focal point FP1. Received signals R1 through R8 detected by the transducer elements 11-1 through 11-8 are supplied to the delay adjustment circuit 22 through the pulser-and-switch circuit 10 and the amplifier-and-AD-converter circuit 12, and are then given respective delays by the delay adjustment circuit 22. In so doing, no delay, for example, may be imposed on the received signals R1 and R8 corresponding to the transducer elements 11-1 and 11-8 situated at the opposite ends. A predetermined first delay is imposed on the received signals R2 and R7 corresponding to the two transducer elements 11-2 and 11-7 that are the second ones from the opposite ends. Further, a second delay which is longer than the first delay is imposed on the received signals R3 and R6 corresponding to the two transducer elements 11-3 and 11-6 that are the third ones from the opposite ends. A third delay which is longer than the second delay is imposed on the received signals R4 and R5 corresponding to the two transducer elements 11-4 and 11-5 that are the fourth ones from the opposite ends. Namely, the 8 received signals corresponding to the transducer elements 11-1 through 11-8 of the transducer array 11 are given respective delays that are symmetrical between the two sides across the center which is situated between the two centrally located elements, such that the closer to the center the transducer element is, the greater the delay is. With this arrangement, the received signals corresponding to the ultrasonic pulse from the focal point FS1 received by the transducer elements 11-1 through 11-8 are aligned at the same position on the time axis for provision to the coherent addition process.

In the case of 8 transducer elements being used for transmission and reception of ultrasonic waves as illustrated in FIG. 2 and FIG. 3, the position of the focal point in the horizontal direction (i.e., the position in the direction in which the transducer elements are aligned) matches the midpoint between the two centrally located transducer elements. As the scan beam is shifted by successively shifting 8 driven transducer elements, the focal point of these 8 transducer elements moves by the distance matching the size of one transducer element (or the pitch of the transducer element array). Namely, the distance between two adjacent ultrasonic beams among the plurality of ultrasonic beams that are driven one by one is equal to the pitch of the transducer element array. The ultrasonic imaging apparatus illustrated in FIG. 1 is configured to perform the operation of selectively driving an odd number of transducer elements so as to make the distance between two adjacent ultrasonic beams (i.e., the distance between the focal points of two adjacent scan lines) shorter than the pitch of the transducer element array.

Figure 4:
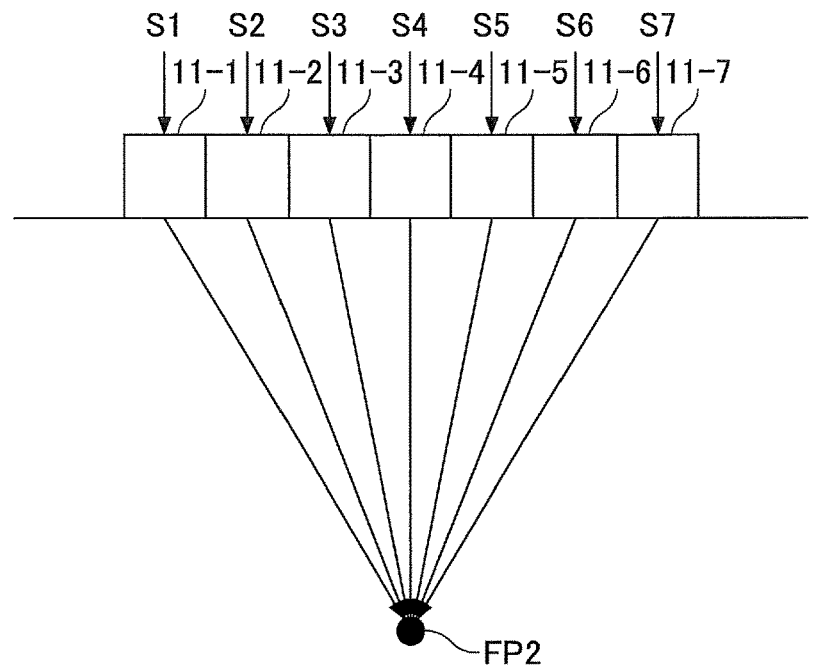
FIG. 4 is a drawing illustrating an example of a transmission operation for which 7 transducer elements are selectively driven.

FIG. 4 is a drawing illustrating an example of a transmission operation for which 7 transducer elements are selectively driven. In FIG. 4, transducer elements 11-1 through 11-7 are 7 consecutive transducer elements among a plurality (e.g., 64) of transducer elements of the transducer array 11 arranged in a line. As pulse voltage signals S1 through S7 are applied to the 7 transducer elements 11-1 through 11-7, respectively, the transducer elements 11-1 through 11-7 transmit an ultrasonic pulse toward a focal point FP2. In so doing, the pulse voltage signals S1 and S7 are first applied to the transducer elements 11-1 and 11-7 situated at the opposite ends, respectively. Upon the passage of a predetermined delay time thereafter, the pulse voltage signals S2 and S6 are applied to the transducer elements 11-2 and 11-6, respectively, which are the second ones from the opposite ends. Upon the passage of a predetermined delay time thereafter, the pulse voltage signals S3 and S5 are applied to the transducer elements 11-3 and 11-5, respectively, which are the third ones from the opposite ends. Upon the passage of a predetermined delay time thereafter, the pulse voltage signal S4 is applied to the centrally located transducer element 11-4. Namely, the transducer elements 11-1 through 11-7 of the transducer array 11 transmit an ultrasonic pulse with respective delays that are symmetrical between the two sides across the centrally located element, such that the closer to the center the transducer element is, the greater the delay is. This arrangement allows the transducer elements 11-1 through 11-7 to transmit an ultrasonic pulse having a wavefront converging toward the focal point FS2.

Figure 5:
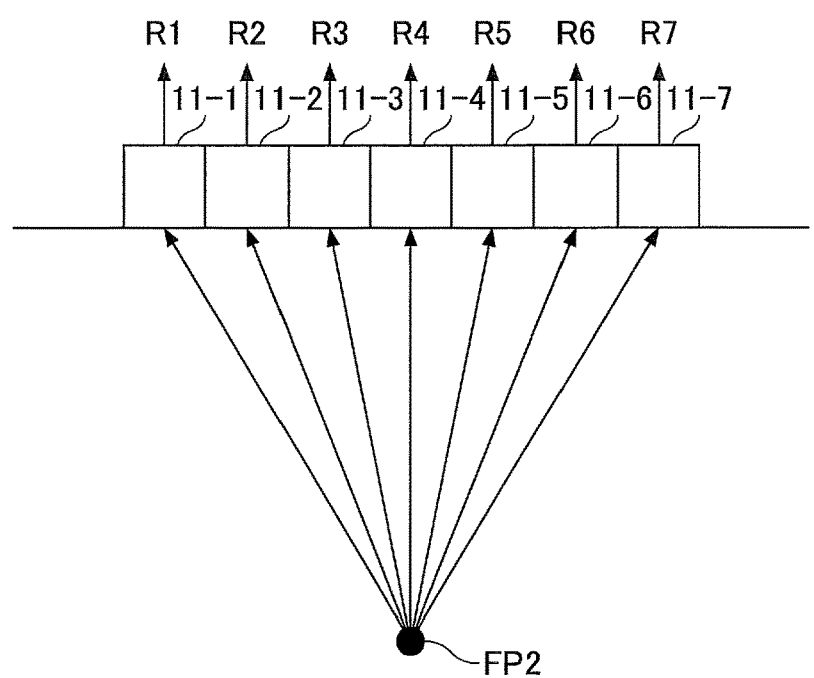
FIG. 5 is a drawing illustrating an example of a reception operation for which 7 transducer elements are selectively driven.

FIG. 5 is a drawing illustrating an example of a reception operation for which 7 transducer elements are selectively driven. In FIG. 5, the transducer elements 11-1 through 11-7, which are 7 consecutive transducer elements among a plurality (e.g., 64) of transducer elements of the transducer array 11 arranged in a line, receive echoes from the focal point FP2. Received signals R1 through R7 detected by the transducer elements 11-1 through 11-7 are supplied to the delay adjustment circuit 22 through the pulser-and-switch circuit 10 and the amplifier-and-AD-converter circuit 12, and are then given respective delays by the delay adjustment circuit 22. In so doing, no delay, for example, may be imposed on the received signals R1 and R7 corresponding to the transducer elements 11-1 and 11-7 situated at the opposite ends. A predetermined first delay is imposed on the received signals R2 and R6 corresponding to the two transducer elements 11-2 and 11-6 that are the second ones from the opposite ends. Further, a second delay which is longer than the first delay is imposed on the received signals R3 and R5 corresponding to the two transducer elements 11-3 and 11-5 that are the third ones from the opposite ends. Moreover, a third delay which is longer than the second delay is imposed on the received signal R4 corresponding to the centrally located transducer element 11-4. Namely, the 7 received signals corresponding to the transducer elements 11-1 through 11-7 of the transducer array 11 are given respective delays that are symmetrical between the two sides across the centrally located element, such that the closer to the center the transducer element is, the greater the delay is. With this arrangement, the received signals corresponding to the ultrasonic pulse from the focal point FS2 received by the transducer elements 11-1 through 11-7 are aligned at the same position on the time axis for provision to the coherent addition process.

In the case of the 7 transducer elements 11-1 through 11-7 being used for transmission and reception of ultrasonic waves as illustrated in FIG. 4 and FIG. 5, the position of the focal point in the horizontal direction (i.e., the position in the direction in which the transducer elements are aligned) matches the midpoint of the centrally located transducer element 11-4. Namely, the focal point moves by the distance matching half the size of one transducer element (or the pitch of the array elements) relative to the position of the focal point observed when the 8 transducer elements 11-1 through 11-8 are used for transmission and reception of ultrasonic waves as illustrated in FIG. 2 and FIG. 3. Namely, the distance between two adjacent ultrasonic beams among the plurality of ultrasonic beams that are driven one by one is set equal to half the pitch of the transducer element array.

Figure 6:
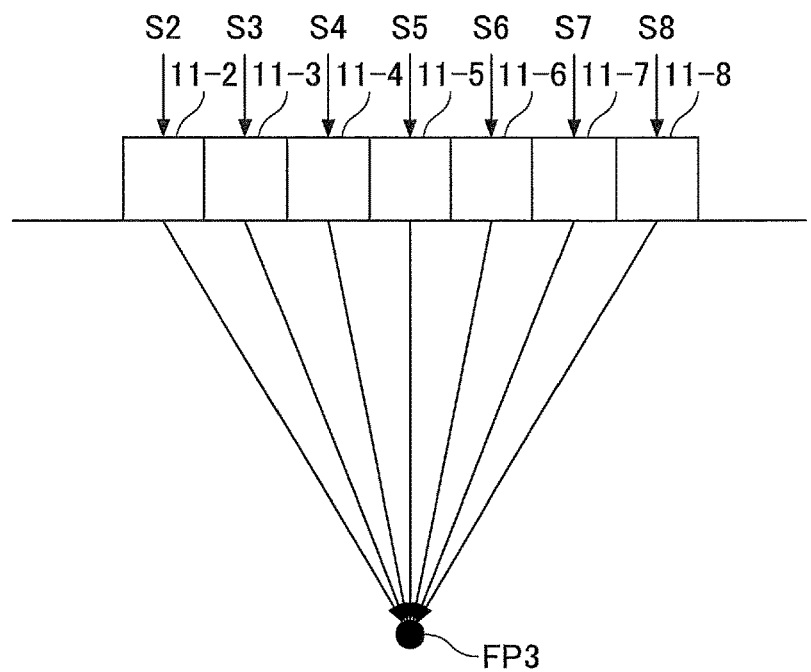
FIG. 6 is a drawing illustrating another example of a transmission operation for which 7 transducer elements are selectively driven.

FIG. 6 is a drawing illustrating another example of a transmission operation for which 7 transducer elements are selectively driven. In FIG. 6, the transducer elements 11-2 through 11-8 are 7 consecutive transducer elements among a plurality (e.g., 64) of transducer elements of the transducer array 11 arranged in a line. The differences of ultrasonic pulse transmission timings between the 7 transducer elements are the same as those of the example illustrated in FIG. 4. Use of the 7 transducer elements 11-2 through 11-8 serves to form a focal point FC3 at the position of the centrally located transducer element 11-5.

Figure 7:
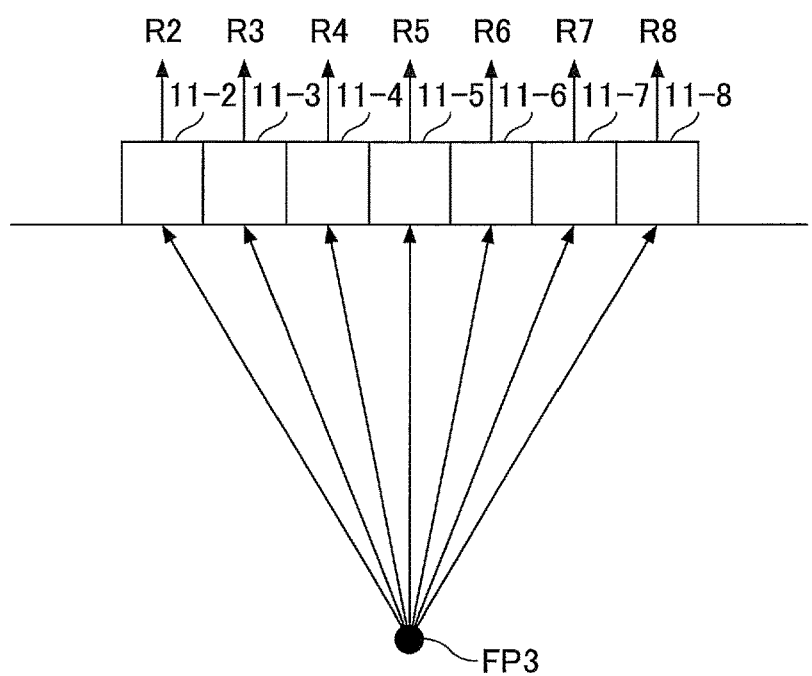
FIG. 7 is a drawing illustrating another example of a reception operation for which 7 transducer elements are selectively driven.

FIG. 7 is a drawing illustrating another example of a reception operation for which 7 transducer elements are selectively driven. In FIG. 7, the transducer elements 11-2 through 11-8, which are 7 consecutive transducer elements among a plurality (e.g., 64) of transducer elements of the transducer array 11 arranged in a line, receive echoes from the focal point FP3. The differences of delay times between the 7 receives signals from the 7 transducer elements are the same as those of the example illustrated in FIG. 5.

The 7 transducer elements 11-1 through 11-7 may be used for the first scan as illustrated in FIG. 4 and FIG. 5, and, then, the 8 transducer elements 11-1 through 11-8 may be used for the second scan as illustrated in FIG. 2 and FIG. 3, which serves to make the distance between scan lines equal to half the pitch of the elements. Further, the 8 transducer elements 11-1 through 11-8 may be used for the second scan as illustrated in FIG. 2 and FIG. 3, and, then, the 7 transducer elements 11-2 through 11-8 may be used for the third scan as illustrated in FIG. 6 and FIG. 7, which serves to make the distance between scan lines equal to half the pitch of the elements. In this manner, the first operation of selectively driving an odd number of transducer elements and the second operation of selectively driving an even number of transducer elements are alternately performed to enable the provision of resolution matching half the size of a transducer element (or the pitch of the array).

Figure 8:
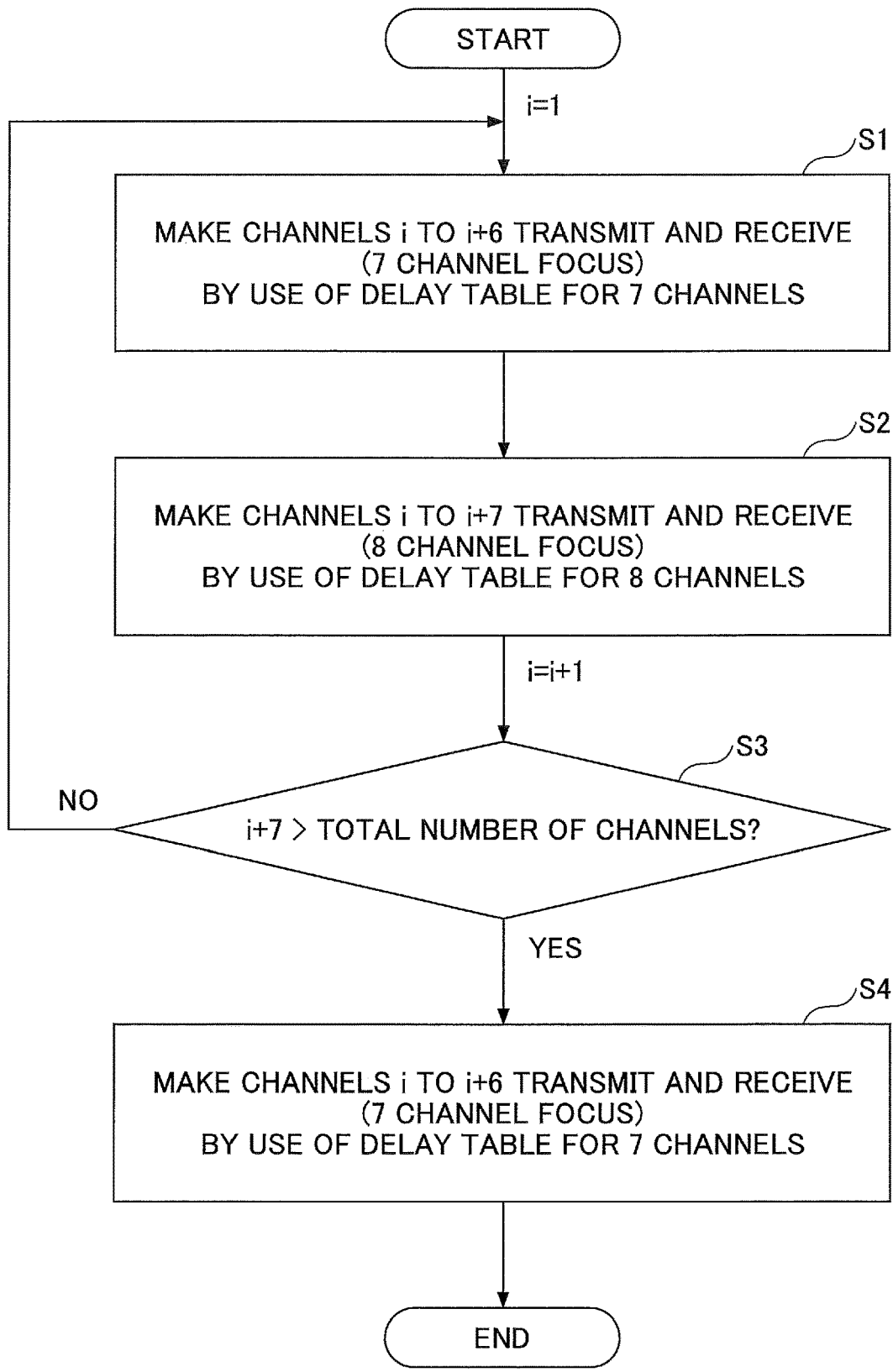
FIG. 8 is a flowchart illustrating the operation of scanning an ultrasonic beam in the ultrasonic imaging apparatus illustrated in FIG. 1.

FIG. 8 is a flowchart illustrating the operation of scanning an ultrasonic beam in the ultrasonic imaging apparatus illustrated in FIG. 1. In this flowchart, the numbers of selectively driven transducer elements are 7 and 8. In the process illustrated in this flowchart, a delay table for 7 channels and a delay table for 8 channels are used. FIG. 9 is a drawing illustrating an example of the delay table for 8 channels. FIG. 10 is a drawing illustrating an example of the delay table for 7 channels. These delay tables will be described later in detail.

By referring to FIG. 8 again, a variable i is set to an initial value "1" at the onset of the operation of this flowchart. At step S1, subsequently, the 7 channels i through i+6 perform transmission and reception. Namely, under the control of the timing control circuit 21, the pulser-and-switch circuit 10 of the ultrasonic imaging apparatus illustrated in FIG. 1 selectively drives i-th through i+6-th transducer elements of the transducer array 11, thereby causing ultrasonic pulses to be transmitted and received. At this time, the delay table for 7 channels is used to set the delay times for transmission from 7 transducer elements (i.e., the settings of delay times of pulse voltage signals with respect to the respective channels) and to set the delay times for the respective channels of received signals received by the 7 transducer elements.

FIG. 10 illustrates an example of the delay times of 7 channels for different focal point positions (depths). In order to transmit and receive an ultrasonic pulse such as to have a focus at a desired depth, the delay times for this depth as given in the delay table illustrated in FIG. 10 are used for both the timing control of pulse voltage signals for transmission of an ultrasonic pulse and the delay control of received signals. Namely, in the case of transmission with a focus point at a depth of 40 mm, for example, the pulse voltage signals applied to the i-th through i+6-th transducer elements are given with delays equal to 0, 17.78, 28.45, 32.01, 28.45, 17.78, and 0, respectively. Further, in the case of reception with a focus point at a depth of 40 mm, for example, the received signals from the i-th through i+6-th transducer elements are given with delays equal to 0, 17.78, 28.45, 32.01, 28.45, 17.78, and 0, respectively.

The deeper the position of the focal point of interest is, the smaller the differences in the distance from the 7 transducer elements to the focal point between the channels are, and, thus, the smaller also the differences between the delays of the 7 channels given in the delay table are. In opposite terms, the shallower the position of the focal point of interest is, the greater the differences in the distance from the 7 transducer elements to the focal point between the channels are, and, thus, the greater also the differences between the delays of the 7 channels given in the delay table are.

With respect to the setting of a depth in the ultrasonic imaging apparatus illustrated in FIG. 1, an image having a focus at a depth set in advance may be collected and displayed in order to obtain an ultrasound B-mode image, for example. Alternatively, in order to obtain an ultrasound B-mode image, images having focuses at different depths may be collected, and portions having high image quality around the focus points may be extracted from the respective images, followed by combining the high-image-quality portions of the respective images for image synthesis, thereby creating an image the entirety of which has high image quality.

By referring to FIG. 8 again, at step S2, 8 channels i through i+7 perform transmission and reception. Namely, under the control of the timing control circuit 21, the pulser-and-switch circuit 10 of the ultrasonic imaging apparatus illustrated in FIG. 1 selectively drives i-th through i+7-th transducer elements of the transducer array 11, thereby causing ultrasonic pulses to be transmitted and received. At this time, the delay table for 8 channels is used to set the delay times for transmission from 8 transducer elements (i.e., the settings of delay times of pulse voltage signals with respect to the respective channels) and to set the delay times for the respective channels of received signals received by the 8 transducer elements.

FIG. 9 illustrates an example of the delay times of 8 channels for different focal point positions (depths). The technical significance of the delay times given in this delay table is the same as in the case of FIG. 10. Namely, in order to transmit and receive an ultrasonic pulse such as to have a focus at a desired depth, the delay times for this depth as given in the delay table illustrated in FIG. 9 are used for both the timing control of pulse voltage signals for transmission of an ultrasonic pulse and the delay control of received signals.

By referring to FIG. 8 again, at step S3, a check is made as to whether i+7 is greater than the total number of channels. It may be noted that the variable i is incremented by one before step S3. The total number of channels is the total number of transducer elements provided in the transducer array 11, and is 64 in the example of the ultrasonic imaging apparatus illustrated in FIG. 1. In the case of i+7 being not greater than the total number of channels, the procedure returns to step S1 to perform the process at step S1 and the processes of the subsequent steps.

In the case of i+7 being greater than the total number of channels, the procedure process to step S4, at which 7 channels i through i+6 perform transmission and reception. At this time, the delay table for 7 channels is used to set the delay times for transmission from 7 transducer elements and to set the delay times for the respective channels of received signals received by the 7 transducer elements.

With the operation noted above, a scan of an ultrasonic beam by the ultrasonic imaging apparatus comes to an end. Namely, a scan of an ultrasonic beam in the horizontal direction (i.e., in the direction in which the transducer elements are aligned) comes to an end.

Figure 11:
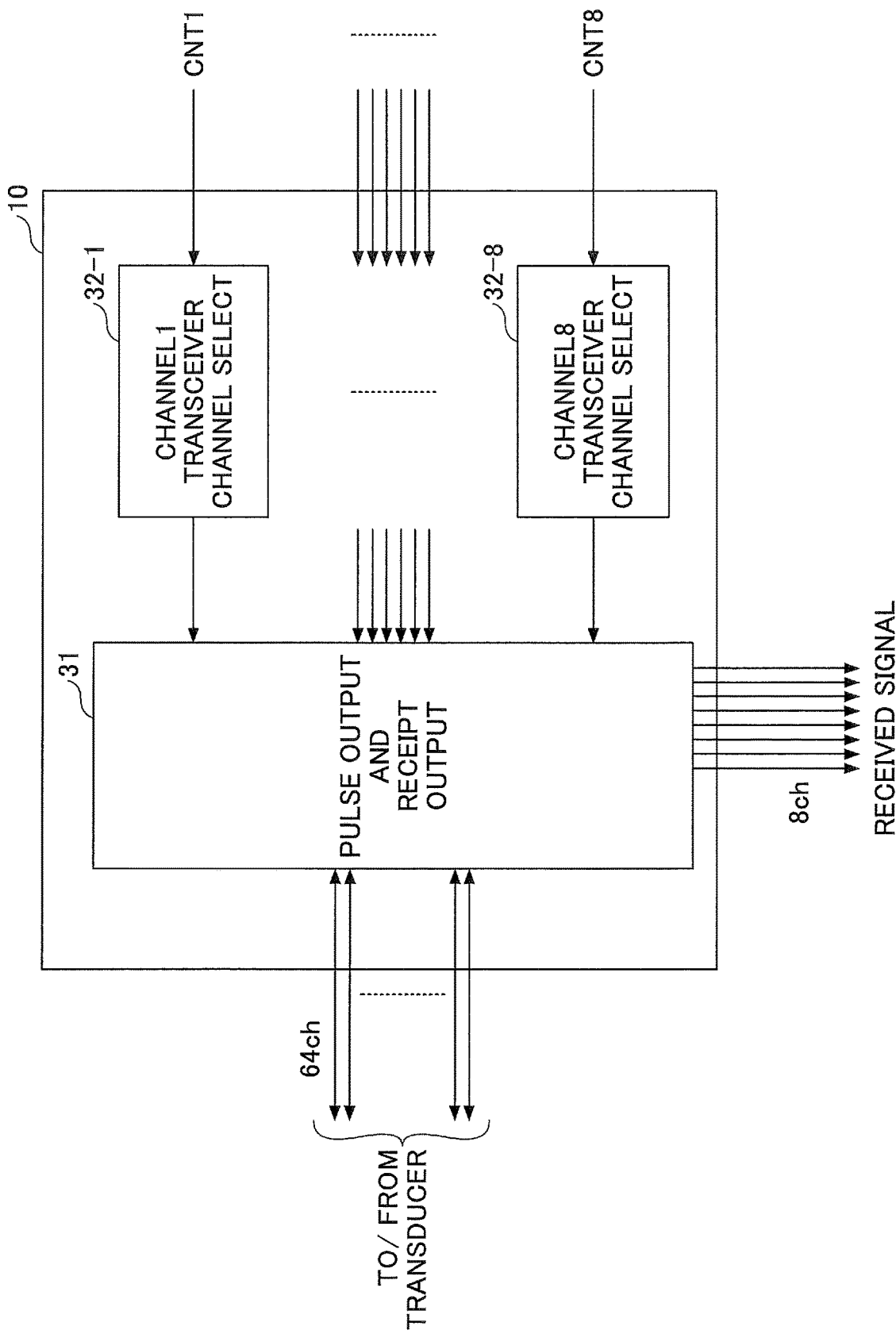
FIG. 11 is a drawing illustrating an example of the configuration of a pulser-and-switch circuit.

FIG. 11 is a drawing illustrating an example of the configuration of the pulser-and-switch circuit 10. The pulser-and-switch circuit 10 illustrated in FIG. 11 includes a pulse-output and reception-output circuit 31 and transceiver-channel select circuits 32-1 through 32-8.

The transceiver-channel select circuits 32-1 through 32-8 receive control signals CNT1 through CNT8, respectively, from the timing control circuit 21 of the digital signal processing circuit 13 illustrated in FIG. 1. The control signals CNT1 through CNT8 may include information indicative of a channel number to be selected and information indicative of a delay time of a channel. The information indicative of a delay time of a channel may be produced by the timing control circuit 21 referring to the delay tables illustrated in FIG. 9 and FIG. 10. The transceiver-channel select circuits 32-1 through 32-8 control the pulse-output and reception-output circuit 31 in response to the control signals CNT1 through CNT8, respectively, so that the pulse-output and reception-output circuit 31 drives the transducer elements having the selected channel numbers with the designated delay times, respectively. Specifically, the pulse-output and reception-output circuit 31 selectively drives 7 transducers in the first operation, and selectively drives 8 transducers in the second operation.

The pulse-output and reception-output circuit 31 also receives received signals from the transducer elements having the selected channel numbers under the control of the transceiver-channel select circuits 32-1 through 32-8, thereby supplying the received signals to the amplifier-and-AD-converter circuit 12 (see FIG. 1). In the first operation, the received signals from the 7 selected transducers are supplied from the pulse-output and reception-output circuit 31 to the amplifier-and-AD-converter circuit 12. The signal paths from the pulse-output and reception-output circuit 31 to the amplifier-and-AD-converter circuit 12 are 8 channels, so that one of the signal paths does not carry a received signal in the first operation. In the second operation, the received signals from the 8 selected transducers are supplied from the pulse-output and reception-output circuit 31 to the amplifier-and-AD-converter circuit 12.

Figure 12:
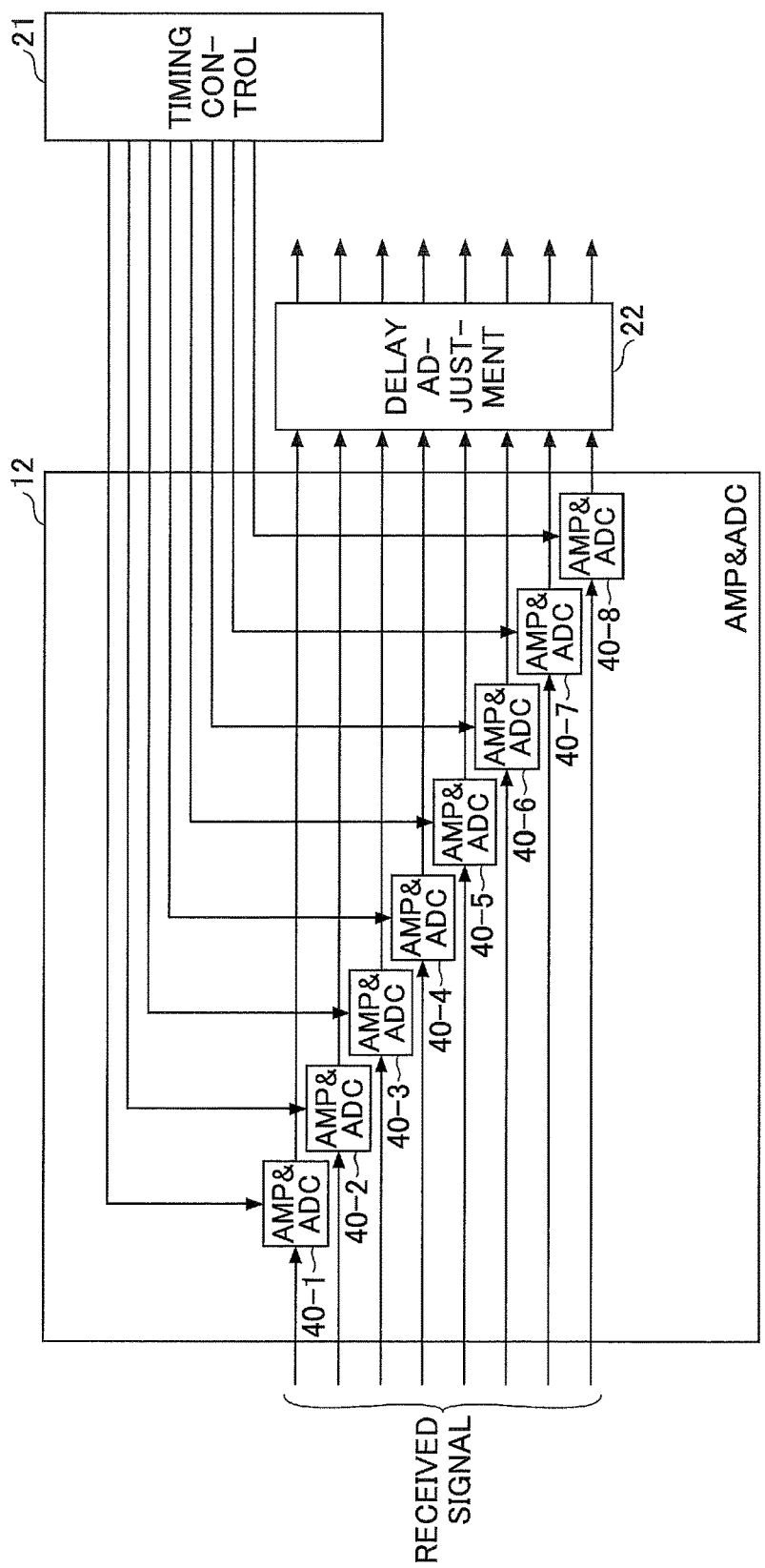
FIG. 12 is a drawing illustrating an example of the configuration of an amplifier-and-AD-converter circuit.

FIG. 12 is a drawing illustrating an example of the configuration of the amplifier-and-AD-converter circuit 12. The amplifier-and-AD-converter circuit 12 illustrated in FIG. 12 includes a plurality of AMP&ADCs 40-1 through 40-8 having an amplification function and an AD conversion function.

The AMP&ADCs 40-1 through 40-8 receive the received signals from the pulser-and-switch circuit 10, and amplify these received signals. The AMP&ADCs 40-1 through 40-8 further convert the amplified received signals from analog signals into digital signals, followed by supplying the converted received signals to the delay adjustment circuit 22 of the digital signal processing circuit 13. In the first operation, 7 AMP&ADSs (e.g., 40-1 through 40-7) are driven among the AMP&ADCs 40-1 through 40-8. In the second operation, the 8 AMP&ADSs are driven among the AMP&ADCs 40-1 through 40-8. In the first operation, the operation of one AMP&ADC among the AMP&ADCs 40-1 through 40-8 is suspended, thereby reducing power consumption accordingly.

Figure 13:
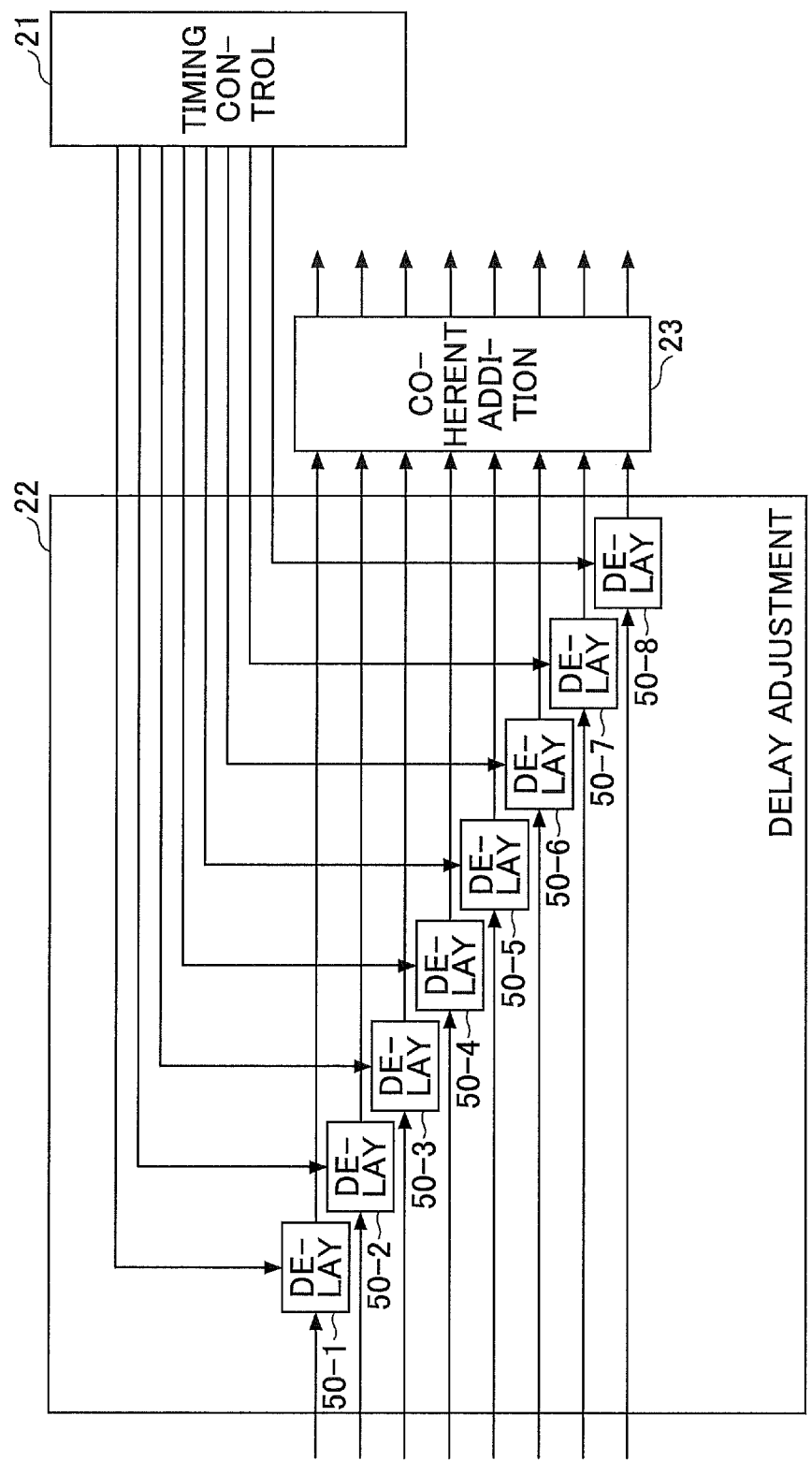
FIG. 13 is a drawing illustrating an example of the configuration of a delay adjustment circuit.

FIG. 13 is a drawing illustrating an example of the configuration of the delay adjustment circuit 22. The delay adjustment circuit 22 illustrated in FIG. 13 includes delay circuits 50-1 through 50-8.

The delay circuits 50-1 through 50-8 receive 8 or 7 received signals from the amplifier-and-AD-converter circuit 12, and also receive delay time data for setting delay times from the timing control circuit 21. The delay circuits 50-1 through 50-8 delay the respective received signals with delay times set in response to the delay time data. In the case of received signals being supplied from 7 transducer elements in the first operation, the delay times given in the delay table for 7 channels illustrated in FIG. 10 may be set in the delay circuits 50-1 through 50-8. In the case of received signals being supplied from 8 transducer elements in the second operation, the delay times given in the delay table for 8 channels illustrated in FIG. 9 may be set in the delay circuits 50-1 through 50-8. Namely, the delays of the received signals delayed by the delay circuits 50-1 through 50-8 are set to different values between the first operation and the second operation. This arrangement enables the subsequent coherent addition circuit 23 to perform proper coherent addition with timing being aligned. As for focal depth, the data indicative of delay times corresponding to a focal depth arranged for the received signals that are to be subjected to such delay processing may be extracted from the delay table illustrated in FIG. 9 or FIG. 10, followed by supplying delay time data for setting these delay times to the delay circuits 50-1 through 50-8.

Figure 14:
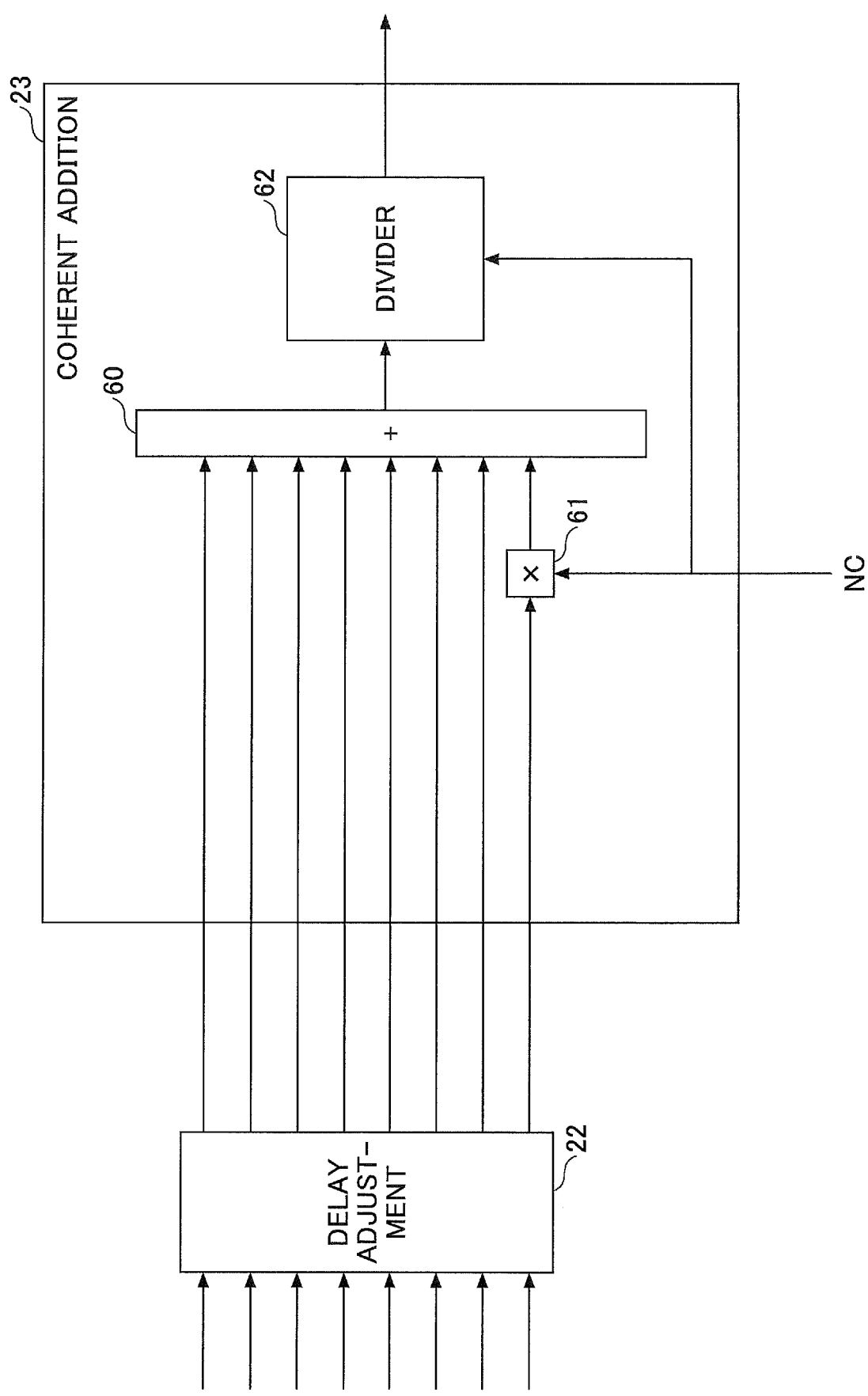
FIG. 14 is a drawing illustrating an example of the configuration of a coherent addition circuit.

FIG. 14 is a drawing illustrating an example of the configuration of the coherent addition circuit 23. The coherent addition circuit 23 illustrated in FIG. 14 includes an adder 60, a multiplier 61, and a divider 62. The adder 60 receives the received signals properly delayed by the delay adjustment circuit 22. 7 received signals from 7 transducer elements are supplied in the first operation, and 8 received signals from 8 transducer elements are supplied in the second operation.

An add-quantity control signal NC, which is supplied from the timing control circuit 21, assumes a value of "0" in the first operation, for example, and assumes a value of "1" in the second operation, for example. One of the 8 channels input into the adder 60 has the multiplier 61 inserted therein, which receives the add-quantity control signal NC. The multiplier 61 multiplies the received signal supplied from the delay adjustment circuit 22 by the add-quantity control signal NC, thereby outputting "0" in the first operation and outputting the same signal as the supplied received signal in the second operation. When only 7 transducer elements are used for transmission and reception by the transducer array 11 in the first operation, the signal of the eighth channel may be completely zero without any noise. In such a case, the multiplier 61 does not have to be necessarily provided.

The adder 60 adds up the signals of the 8 channels. The output of the multiplier 61 is zero in the first operation, so that the adder 60 actually adds up the signals of the 7 channels. Namely, the adder 60 adds up 7 received signals from 7 transducer elements in the first operation, and adds up 8 received signals from 8 transducer elements in the second operation. The result of addition is supplied to the divider 62.

The divider 62 receives the result of addition from the adder 60, and also receives the add-quantity control signal NC from the timing control circuit 21. The divider 62 divides the result of addition by 7 in the case of the add-quantity control signal NC being "0", and divides the result of addition by 8 in the case of the add-quantity control signal NC being "1". Namely, the divider 62 divides the result of addition by 7 in the case of receiving 7 received signals from 7 transducer elements in the first operation, and divides the result of addition by 8 in the case of receiving 8 received signals from 8 transducer elements in the second operation. Dividing by a number equal to the number of signals to be added serves to normalize the amplitude of a signal resulting from the division, which ensures that signals obtained in the first operation and the second operation have comparative amplitudes with each other even though the number of signals added by coherent addition differs between the first operation and the second operation.

The description of the above-noted embodiment has been directed to an example in which the odd number of channels driven in the first operation is 7, and the even number of channels driven in the second operation is 8. These numbers are examples only. Which one of the number in the first operation and the number in the second operation is greater than the other does not matter. The difference between the number in the first operation and the number in the second operation does not have to be necessarily "1". For example, the odd number of channels driven in the first operation may be 9, and the even number of channels driven in the second operation may be 8. Alternatively, for example, the odd number of channels driven in the first operation may be 5, and the even number of channels driven in the second operation may be 8. The numbers of channels driven in the first and second operations may be 5 and 6, respectively, for a close focal point while the numbers of channels driven in the first and second operations may be 7 and 8, respectively, for a faraway focal point. In this manner, the numbers may be changed according to the focus distance.

The description of the above-noted embodiment has been directed to an example in which an ultrasonic pulse is transmitted and received with respect to an odd number of channels in the first operation, and an ultrasonic pulse is transmitted and received with respect to an even number of channels in the second operation. Notwithstanding this, the number of driven channels does not have to be necessarily an odd number in order to position the focal point between the two transducer elements. Driving an even number of transducer elements with asymmetric suitable delays may cause the focal point to be situated between two transducer elements. An even number of transducer elements may be driven in such a manner while driving an odd number of AMP&ADCs the number of which is smaller than the number of driven transducer elements, followed by providing an odd number of signals for addition by the coherent addition circuit 23. This arrangement also provides the advantages of improvement in resolution and reduction in power consumption to some extent.

According to at least one embodiment, resolution is increased to improve image quality for an ultrasonic imaging apparatus.

Further, although the present invention has been described with reference to the embodiments, the present invention is not limited to these embodiments, and various variations and modifications may be made without departing from the scope as defined in the claims.

What is claimed is:

1. An ultrasonic imaging apparatus, comprising:
   a plurality of transducers aligned in an array;
   a select circuit configured to cause transducers selected from the plurality of transducers to transmit an ultrasonic pulse and receive received signals, respectively; and
   a digital signal processing circuit configured to perform a first operation of adding up an odd number of the received signals, arranged in an order corresponding to the aligned array, with delays that are symmetrical between two sides across a center that is a centrally located signal, and to perform a second operation of adding up an even number of the received signals, arranged in an order corresponding to the aligned array, with delays that are symmetrical between two sides across a center that is situated between two centrally located signals,
   wherein the digital signal processing circuit is further configured to divide a result of adding up the odd number of the received signals by a number equal to the odd number and to divide a result of adding up the even number of the received signals by a number equal to the even number.

2. The ultrasonic imaging apparatus as claimed in claim 1, further comprising a plurality of AD converters configured to convert the received signals from analog signals into digital signals and to supply the converted received signals to the digital signal processing circuit, wherein as many AD converters as the odd number among the plurality of AD converters are driven in the first operation, and as many AD converters as the even number among the plurality of AD converters are driven in the second operation.

3. The ultrasonic imaging apparatus as claimed in claim 1, wherein as many transducers as the odd number are selectively driven by the select circuit in the first operation, and as many transducers as the even number are selectively driven by the select circuit in the second operation.

4. The ultrasonic imaging apparatus as claimed in claim 1, wherein the digital signal processing circuit includes:
   a delay adjustment circuit configured to delay the received signals with respective delays; and
   a coherent addition circuit configured to add up the received signals delayed by the delay adjustment circuit,
   wherein the delays of the received signals imposed by the delay adjustment circuit are set to different values between the first operation and the second operation.

5. An ultrasonic imaging apparatus comprising a digital signal processing circuit configured to alternately perform a first operation and a second operation,
   the first operation coherently adding an odd number of received signals obtained by causing an odd number of transducers among a plurality of transducers aligned in a line to transmit and receive ultrasonic waves, and
   the second operation coherently adding an even number of received signals obtained by causing an even number of transducers among the plurality of transducers to transmit and receive ultrasonic waves,
   wherein the digital signal processing circuit is further configured to divide a result of adding up the odd number of the received signals by a number equal to the odd number and to divide a result of adding up the even number of the received signals by a number equal to the even number.

6. A method of controlling an ultrasonic imaging apparatus, comprising:
   causing transducers selected from a plurality of transducers aligned in an array to transmit an ultrasonic pulse and receive first received signals, respectively;
   adding up an odd number of the first received signals arranged in an order corresponding to the aligned array with delays that are symmetrical between two sides across a center that is a centrally located signal;
   causing transducers selected from the plurality of transducers aligned in an array to transmit an ultrasonic pulse and receive second received signals, respectively;
   adding up an even number of the second received signals arranged in an order corresponding to the aligned array with delays that are symmetrical between two sides across a center that is situated between two centrally located signals; and
   dividing a result of adding up the odd number of the first received signals by a number equal to the odd number and dividing a result of adding up the even number of the second received signals by a number equal to the even number.

* * * * *